United States Patent [19]

Niiyama et al.

[11] Patent Number: 4,795,707
[45] Date of Patent: Jan. 3, 1989

[54] ELECTROCHEMICAL SENSOR HAVING THREE LAYER MEMBRANE CONTAINING IMMOBILIZED ENZYMES

[75] Inventors: Yasusi Niiyama; Kenshi Sugahara, both of Katsuta, Japan

[73] Assignee: Hitachi, Ltd., Tokyo, Japan

[21] Appl. No.: 802,193

[22] Filed: Nov. 25, 1985

[30] Foreign Application Priority Data

Nov. 27, 1984 [JP] Japan ............................ 59-249917

[51] Int. Cl.$^4$ .................. C12M 1/40; C12N 11/02; C12N 11/14; G01N 27/26
[52] U.S. Cl. .............................. 435/288; 204/403; 435/174; 435/177; 435/817
[58] Field of Search ............ 435/174, 177, 179, 180, 435/182, 817, 288; 204/403

[56] References Cited

U.S. PATENT DOCUMENTS

| | | | |
|---|---|---|---|
| 4,172,765 | 10/1979 | Keyes | 435/817 X |
| 4,240,889 | 12/1980 | Yoda et al. | 435/817 X |
| 4,307,195 | 12/1981 | Karasama et al. | 435/179 X |
| 4,460,686 | 7/1984 | Hartmeier | 435/177 X |
| 4,579,642 | 4/1986 | Niiyama et al. | 204/403 |
| 4,581,336 | 4/1986 | Malloy et al. | 204/403 X |

FOREIGN PATENT DOCUMENTS 0150656  9/1981  Fed. Rep. of Germany ...... 435/817

OTHER PUBLICATIONS

Therenot et al., Analytical Chemistry, vol. 51, No. 1, 1979, pp. 96–100.

Primary Examiner—David M. Naff
Attorney, Agent, or Firm—Antonelli, Terry & Wands

[57] ABSTRACT

An electrochemical sensor is formed having a working electrode for detecting hydrogen peroxide surrounded by a cylinder portion, and with an enzymecontaining membrane at its tip. The membrane has a porous layer permeable to hydrogen peroxide between a layer containing an immobilized enzyme capable of decomposing hydrogen peroxide and a layer containing an immobilized enzyme capable of decomposing a substrate to form hydrogen peroxide. The cylinder portion is embedded in the layer containing the hydrogen peroxide decomposing enzyme and surrounds the working electrode such that the electrode is in contact with the porous layer but is not in contact with the layer containing the hydrogen peroxide decomposing enzyme. The layer containing the hydrogen peroxide forming enzyme is on a side of the porous layer opposite the electrode so as not to contact the electrode. Activity of the hydrogen peroxide decomposing enzyme is no more than one-fourth of the activity of the hydrogen peroxide forming enzyme.

5 Claims, 2 Drawing Sheets

ELECTROCHEMICAL SENSOR HAVING THREE LAYER MEMBRANE CONTAINING IMMOBILIZED ENZYMES

BACKGROUND OF THE INVENTION

This invention relates to an electrochemical sensor, and particularly to an electrochemical sensor based on a conbination of a membrane having an immobilized enzyme capable of decomposing a substrate in a sample, thereby forming hydrogen peroxide ($H_2O_2$) and an electrode capable of detecting hydrogen peroxide.

It is known that the conventional electrochemical sensor can quantitatively determine trace components such as glucose, urea, cholesterol, etc. contained in a body fluid, living body tissue, food, etc. with a good selectivity.

The electrochemical sensor has such a distinguished characteristic that no special reagent is required, and its application field has been expanded with the recent development of living body catalyst-immobilizing technique.

According to the structure of the electrochemical sensor, a resin layer having an immobilized living body catalyst consisting of an enzyme is provided on the outer peripheral surface of the sensor, and a working electrode for determining a concentration of the reaction product formed by reaction of a substrate in a sample with the living body catalyst by detecting an electrical change (e.g. changes in potential and current) is provided inside the sensor.

An example of the conventional and ordinary immobilized enzyme electrode is disclosed, for example, in Japanese Patent Application Kokai (Laid-open) No. 55-98347, where a working electrode is extended to the center of an enzyme electrode so that the tip end of the working electrode can come in substantial contact with the surface of the immobilized enzyme membrane.

According to a method for determining a substrate in a sample by an immobilized enzyme electrode, electrode-active substances such as hydrogen peroxide, ammonium ions, carbon dioxide gas, etc., formed by reaction of the enzyme with the substrate when the enzyme electrode is brought in contact with a sample solution, are amperometrically or potentiometrically detected to determine unknown quantities of substances contained in the sample solution. That is, the current or electromotive force generated on the electrodes is proportional to a quantity of a substance to be determined in a sample, and thus the substance in the example can be quantitatively determined from a working curve prepared in advance.

An application example of said enzyme electrode is a glucose electrode practically used for amperometrically determining glucose in blood or urine by decomposing the glucose to hydrogen peroxide by immobilized glucose oxidase and measuring the concentration of hydrogen peroxide with an internal electrode having a novel metal as a working electrode, to which about 0.6 V is applied in advance. The glucose electrode is incorporated into a unifunctional apparatus mainly based on a batch-type measurement, and is extensively used as an important information source for the diabetes mellitus and other diseases.

To meet the requirements for rapidity in the quantitative determination of a glucose concentration, a glucose sensor has been just applied to a flow-through type analyzer [e.g. "Analytical Chemistry, Vol. 51 No. 1 (1979) pages 96–100"]. The flow-through type determination comprises introducing a sample of blood or urine from a patient into a carrier liquid, and bringing the carrier liquid containing the sample in contact with a glucose electrode provided in the flow passage to quantitatively determine the concentration of glucose in the sample.

The present inventors have found that an application of the immobilized enzyme electrode as disclosed in said Japanese Patent Application Kokai (Laid-open) No. 55-98347 to a flow-through type analyzer as such has various practical problems. One of the problems is a phenomenon that, when a glucose electrode is left in contact with a liquid for a long time, an abnormally high measured value is obtained in the successive measurement of an actual sample. If an operator carries out analytical operation without any knowledge of the phenomenon found by the present inventors, elevation of the base line is induced to lower the accuracy of measurement.

SUMMARY OF THE INVENTION

An object of the present invention is to provide an enzyme electrode with a high accuracy of measurement even if a membrane containing an enzyme capable of forming hydrogen peroxide is used.

Another object of the present invention is to provide an enzyme electrode capable of reducing the elevation of base line even after the measurement action is discontinued for a long time.

Another object of the present invention is to provide an enzyme electrode capable of inhibiting hydrogen peroxide from staying in the vicinity of the working electrode capable of detecting hydrogen peroxide.

An enzyme electrode according to the present invention has a novel membrane which comprises a layer containing an immobilized enzyme capable of decomposing a substrate in a sample and forming hydrogen peroxide, and a layer containing an immobilized catalase capable of decomposing hydrogen peroxide.

When the measurement action of an enzyme electrode is discontinued and the membrane is kept in contact with a liquid, hydrogen peroxide is gradually formed by the action of the hydrogen peroxide-forming enzyme, and gradually accumulated in the vicinity of the working electrode. The hydrogen peroxide gradually accumulated is in a very small amount, and can be decomposed to disappear by the action of the catalase. Thus, an elevation of base line owing to the remaining hydrogen peroxide can be suppressed thereby even when the measurement action is restarted.

DETAILED DESCRIPTION OF THE PREFERRED EMBODIMENTS

Figure 1:
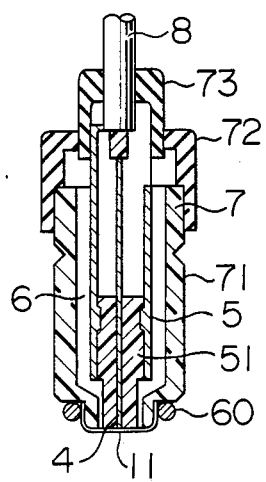
FIG. 1 is a cross-sectional view schematically showing the structure of an elecrochemical sensor according to one embodiment of the present invention.

On a glucose electrode having a glucose oxidase (GOD) immobilized membrane, the following two reactions (1) and (2) take place in the measurement action.

$$\beta\text{-D-glucose} \xrightarrow{\text{GOD}} \text{gluconic acid} + H_2O_2 \quad (1)$$

$$H_2O_2 \longrightarrow O_2 + 2e^- + 2H^+ \quad (2)$$

Glucose in a sample is decomposed by GOD according to the reaction (1) to form hydrogen peroxide ($H_2O_2$). The thus formed hydrogen peroxide is reduced on a working electrode, to which a potential of about 0.6 V is applied, according to the reaction (2), and hydrogen peroxide no longer remains.

On the other hand, when the measurement action of a sample is completed and when the power source to the glucose electrode is turned off while the membrane of the glucose electrode is kept in contact with the liquid, the potential of about 0.6 V applied to the working electrode is eliminated. A very small amount of glucose present in the liquid is slowly decomposed by GOD, and hydrogen peroxide starts to stay in the internal electrolytic liquid in the vicinity of the working electrode.

Unless the present invention is applied thereto, the hydrogen peroxide, which starts to stay, is gradually accumulated, and generates a strong dark current when the glucose electrode is successively used. Particularly when the measurement action of the analyzer is restarted after the action of the analyzer is discontinued for a long time, it takes more than one hour to stabilize the base line. When the present invention is applied thereto on the other hand, the hydrogen peroxide formed by GOD is decomposed to disappear.

The present invention is applied not only to the glucose electrode, but also to other sensors having an immobilized oxidizing enzyme, for example, various sensors with membranes having immobilized galactose oxidase, alcohol oxidase, pyruvic acid oxidase, amino acid oxidase, and cholesterol oxidase.

According to a desirable embodiment of the present invention, platinum (Pt) is used as a working electrode, but other noble metals such as gold (Au), etc. can be also used.

According to a desirable embodiment of the present invention, palladium (Pd) is used as a counter electrode, but an electrode of silver-silver chloride (Ag/ AgCl) can be also used.

In the present invention, it is important that the catalytic activity should not be too high. For example, in the case of a glucose electrode, if the activity of a catalase layer is so high as to decompose all the hydrogen peroxide formed by the glucose oxidase layer when the electrode is used, the quantitative determination of glucose cannot be carried out. Thus, too high an activity of the catalase layer is not desirable. The activity of a catalase layer must be such as not to deteriorate the reduction reaction of hydrogen peroxide on the working electrode, i.e. the reaction (2). Specifically, it is desirable to suppress the activity of a catalase layer to ¼ or less of the activity of glucose oxidase.

Preferable embodiments of the present invention will be described in detail below, referring to the drawings.

In FIG. 1, a holder 7 has a cylinder 71 and caps 72 and 73. The cylinder 71 is made from polyvinyl chloride resin or acrylic resin, and the caps 72 and 73 are made from polyvinyl chloride resin. A cylinder 51 which supports a working electrode 4 at the lower part is made from epoxy resin. An immobilized enzyme membrane 11 is provided at the tip end of the holder 7, and the working electrode 4 made from a platinum wire is provided against the immobilized enzyme membrane 11. A counter electrode 5 made from palladium is provided at the electrode holder side of working electrode 4 to surround the cylinder 51. An internal electrolytical liquid 6 comprising potassium chloride is filled in the space between the counter electrode 5 and the electrode holder 7. A lead wire 8 is connected to the working electrode 4 to lead the current to an external electric circuit. The membrane is supported by an O-ring 60.

Figure 2:
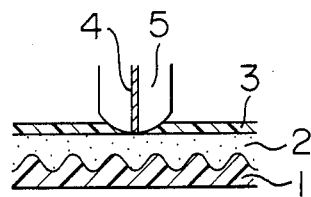
FIG. 2 is a cross-sectional view showing the state of a membrane in the vicinity of the working electrode according to the embodiment of FIG. 1.

The glucose electrode detects the concentration of glucose diluted with a carrier liquid through the immobilized enzyme membrane 11 as a change in the current according to the flow-through measurement procedure, and glucose is quantitatively determined on the basis of a working curve prepared in advance by measuring the current in the external electric circuit. A positional relation between the working electrode 4 and the immobilized enzyme membrane 11 is shown in FIG. 2.

The tip end of the working electrode 4 is ideally in contact with a porous layer 2 having a selective permeability to hydrogen peroxide, but owing to a convenience of practical preparation, a very thin catalase-immobilized layer 3 is provided between the lip end of the working electrode 4 and the porous layer 2. A glucose oxidase layer 1 is provided on the sample-facing side of the porous layer 2, and the catalase-immobilized layer 3 is formed on the working electrode-facing side of the porous layer 2. To keep the contact of the glucose oxidase-immobilized layer 1 with the porous layer 2 strongly, the contact parts are in a corrugated form, and the layers 1 and 2 are chemically bonded to each other by aldehyde groups and amino groups. The working electrode 4 is brought in contact with the porous layer 2 and the resin cylinder 51 around the working electrode is embedded in the catalase-immobilized layer 3.

The working electrode 4 is not in direct contact with the catalase-immobilized layer 3, because, if the working electrode is in direct contact with the catalase-immobilized layer, hydrogen peroxide fails to effectively reach the working electrode when the electrode is used.

Preparation of the immobilized enzyme membrane 11 on which the glucose oxidase and catalase are immobilized will be described in detail below.

PREPARATION OF IMMOBILIZED ENZYME MEMBRANE

At first, a solution consisting of 2.5 g of acetyl cellulose, 40 ml of acetone and 25 ml of formamide was extended on a horizontally supported, flat glass plate to a thickness of 50 μm. The extended solution was left standing for one minute to partially evaporate the solvent off, and then gently dipped in much excess water to conduct solvent extraction for one hour. One hour thereafter, the residue was dried in air to obtain an asymmetrical film having a thickness of 10 μm. The thus obtained asymmetrical film corresponds to a porous layer 2 having a selective permeability to hydrogen peroxide shown in FIG. 2.

Then, glucose oxidase solution was dissolved in a phosphate buffer solution at pH7.0 to obtain an enzyme solution at an enzyme concentration of 10 mg/ml. The thus obtained solution was filtered through the said asymmetric film from the heterogenous layer side under a liquid pressure of 0.5 mpa to fill the glucose oxidase in pores in the heterogenous layer. Then, the homogeneous layer side was treated with a 3% trimethoxyaminosilane solution to form silane groups at the heterogeneous layer side, and then a phosphate buffer solution containing catalase and albumin at pH7.0.and an enzyme concentration of 2 mg/ml was applied thereto to form a catalase-immobilized layer 3 having a thickness of 1 $\mu$m. Finally, the asymmetrical film provided with the glucose oxidase layer and the catalase layer was dipped in a 3% glutaraldehyde solution and kept at 4° C. for 3 hours to carry out cross-linking reaction. The glucose oxidase and catalase were immobilized in the asymmetrical film thereby.

The thus obtained immobilized enzyme membrane 11 was tightly fixed to the working electrode made from platinum as shown in FIG. 1, whereby a glucose electrode was obtained.

Figure 3:
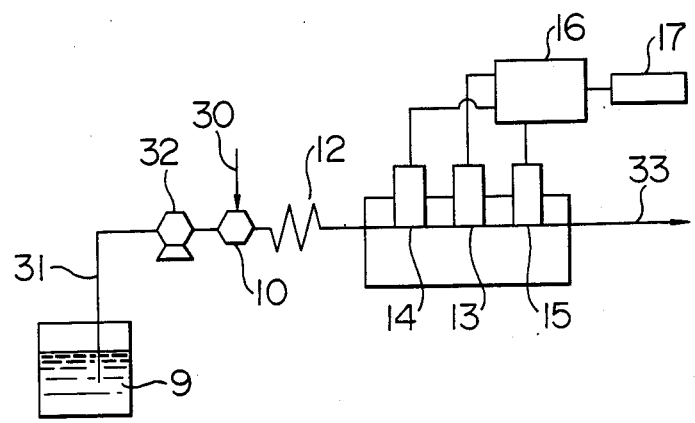
FIG. 3 shows a schematic structure of a flow-through type analyzer using the sensor of FIG. 1.

The thus obtained glucose electrode was placed in a flow-through type analyzer shown in FIG. 3 to find the response characteristics.

In an analyzer shown in FIG. 3, a piping 31 is connected to a carrier buffer solution 9, and a pump 32 and an injection member 10 for a sample 30 are provided in the piping 31. The sample injection member is connected to a mixing coil 12, which is connected to a passage 33 provided with a glucose electrode 14, a urea electrode 13 and a comparative electrode 15. Electrical signals emitted from the individual electrodes are input into an amplifier 16, which is connected to a recorder 17 which records the results of measurement.

A glucose-containing sample was injected into the sample injection member 10 in said flow injection system, and the sample was transferred by the carrier solution 9 by driving the pump 32. Then, the diluted sample was introduced into the passage 33 to determine the concentration of glucose contained in the sample. The working curve is a graph shown in FIG. 4. The output current against the glucose concentration in FIG. 4 can be determined in advance by introducing glucose standard solutions into said flow injection system.

When the glucose electrode having an enzymeimmobilized membrane shown in FIG. 1 was used in said flow-through type analyzer, the output current per unit concentration was a little lowered, as compared with the conventional glucose electrode (without any catalase-immobilized (layer), but a good linear relationship was obtained in the range of 1 to 1,000 mg/dl. Thus, the quantitative determination of glucose contained in the sample had no problem.

Figure 5:
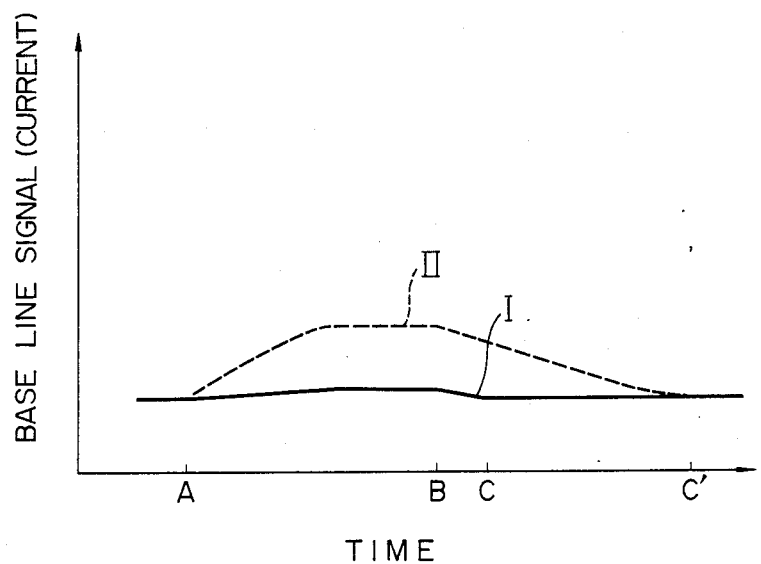
FIG. 5 is a diagram showing a base line comparison between the present electrode (I) and the conventional electrode (II).

This will be described, referring to FIG. 5, where A is a point of measurement action discontinuation of the analyzer and B is a point of measurement action restarting. According to the conventional glucose electrode II (dotted line), the base line is not recovered up to the point C', whereas according to the present glucose electrode I (full line) the base line is recovered at the point C.

Figure 4:
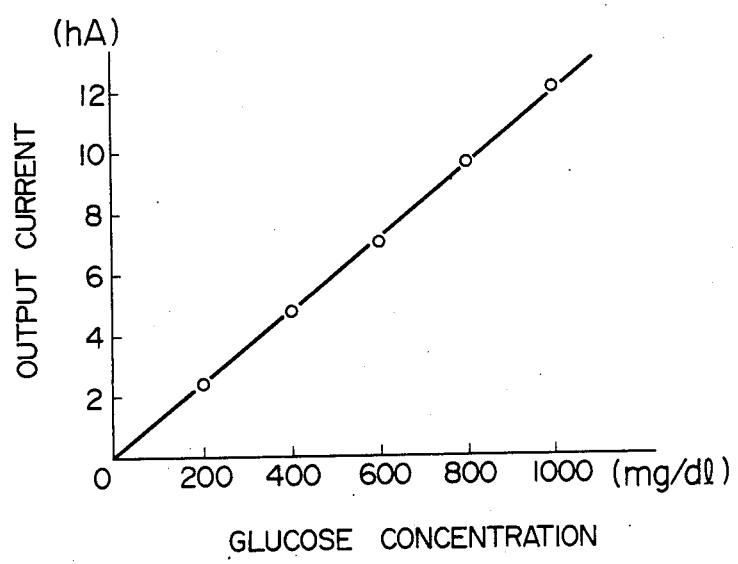
FIG. 4 is a diagram showing the relationship between the glucose concentration and output current according to the present electrode for measuring glucose.

The glucose electrode having the immobilized membrane 11 shown in FIG. 1 can generate an output current with a linearity against the glucose concentration, as shown in FIG. 4, and has no influence by the concentration of glucose in the sample. In the conventional glucose electrode, the base current rapidly increases from 5,000 pico amperes (pA) to 20,000 pA one day after the electric source has been turned off, whereas in the present glucose electrode of FIG. 1, the base current hardly changes, and the time for stabilization of the base line is 15 minutes after the time when the electric power is turned on, which is less than $\frac{1}{4}$ of the time according to the conventional glucose electrode.

Correlation of the present glucose electrode shown in FIG. 2 with the colorimetric procedure was investigated for commercially available, controlled serum. The following good characteristics were found:

Correlation coefficient: 0.984

Regression line: $y=0.95\times 1.4 (n=10)$

Simultaneous reproducibility $CV=1.7\%$ (100 mg/dl)$n=10$

Response time $\tau 95$: 20 seconds at buffer flow rate of 2.0 ml/min.

Thus, the measurement accuracy was better than that of the glucose electrode.

The glucose electrode shown in FIG. 2 has a catalase-immobilized layer 3 on the porous layer 2 having a selective permeability to hydrogen peroxide and thus the amount of hydrogen peroxide generated in accordance with the concentration in glucose in a sample becomes smaller, and thus the glucose oxidase layer can be less changed.

What is claimed is:

1. An electrochemical sensor which comprises a working electrode for detecting hydrogen peroxide surrounded by a cylinder portion, a membrane located at the tip of the working electrode, the membrane having first, second and third layers; the first layer being a porous layer permeable to hydrogen peroxide, the second layer being a layer containing an immobilized enzyme capable of decomposing hydrogen peroxide, and the third layer being a layer containing an immobilized enzyme capable of decomposing a substrate in a sample to form hydrogen peroxide, the first layer being located between the second and third layers; the cylinder portion being embedded in the second layer and surrounding the working electrode such that the working electrode is in substantial contact with the first layer but is not in substantial contact with the second layer and the third layer being located on a side of the first layer opposite to the working electrode so that the third layer does not contact the working electrode but is in substantial contact with said sample wherein the enzyme activity of the enzyme capable of decomposing hydrogen peroxide in the second layer is no more than one-fourth of the enzyme activity of the enzyme capable of forming hydrogen peroxide in the third layer.

2. An electrochemical sensor according to claim 1, wherein the enzyme capable of decomposing hydrogen peroxide is catalase.

3. An electrochemical sensor according to claim 1, wherein the enzyme capable of forming hydrogen peroxide is selected from the group consisting of glucose oxidase, galactose oxidase, alcohol oxidase, pyruvic acid oxidase, amino acid oxidase, and cholesterol oxidase.

4. An electrochemical sensor according to claim 1, wherein a counter electrode is provided on an outer surface of the cylinder portion, the working electrode is made from platinum and the counter electrode is made from palladium.

5. An electrochemical sensor according to claim 2, wherein the catalase activity is less than one-fourth of the enzyme activity of the enzyme capable of forming hydrogen peroxide.

* * * * *